United States Patent [19]

Nakajima et al.

[11] Patent Number: 5,522,890
[45] Date of Patent: Jun. 4, 1996

[54] DEFORMABLE INTRAOCULAR LENS

[75] Inventors: Toshiyuki Nakajima; Toshikazu Kikuchi, both of Tokyo, Japan

[73] Assignee: Canon Staar Co., Inc., Tokyo, Japan

[21] Appl. No.: 271,833

[22] Filed: Jul. 7, 1994

[30] Foreign Application Priority Data

Jul. 15, 1993 [JP] Japan ................... 5-175331

[51] Int. Cl.⁶ .................................................. A61F 2/16
[52] U.S. Cl. ............................................................ 623/6
[58] Field of Search .................................................. 623/6

[56] References Cited

U.S. PATENT DOCUMENTS

| | | | |
|---|---|---|---|
| 4,624,670 | 11/1986 | Bechert, II | 623/6 |
| 4,725,276 | 2/1988 | Bissonette et al. | 623/6 |
| 5,141,507 | 8/1992 | Parekh | 623/6 |
| 5,201,763 | 4/1993 | Brady et al. | 623/6 |

FOREIGN PATENT DOCUMENTS

| | | |
|---|---|---|
| 5-58748 | 2/1983 | Japan. |
| 5-83253 | 8/1992 | Japan. |
| 5-103803 | 4/1993 | Japan. |
| 5-103808 | 4/1993 | Japan. |
| 5-103809 | 4/1993 | Japan. |

*Primary Examiner*—Mary Beth Jones
*Attorney, Agent, or Firm*—Ladas & Parry

[57] ABSTRACT

A deformable intraocular lens which can be inserted in the eye through a smaller incision by being deformed to have a smaller shape. The lens according to the invention has a deformable optical part which is made of an elastic material, the optical part having a lens portion and a peripheral portion surrounding the lens portion. The peripheral portion is thinner than the center of the lens portion. A plurality of supports are made of a flexible material different from the material of the optical part. Each support has an anchor embedded in the optical part for bonding the support to the optical part. A plurality of reinforcing sections having a thickness larger than the peripheral portion of the optical part are provided at a plurality of positions on the peripheral portion of the optical part or in the proximity thereof. The anchors of the supports are embedded in the reinforcing section. The bonding strength between the optical part and the supports is enchanced and the thickness of the optical part is reduced. Thus, the optical part can be deformed in a smaller shape.

20 Claims, 2 Drawing Sheets

DEFORMABLE INTRAOCULAR LENS

BACKGROUND OF THE INVENTION

1. Field of the Invention

The present invention relates to a deformable intraocular lens which is inserted into the eye in place of the natural lens when the latter is physically extracted because of cataracts.

2. Description of the Related Art

It is generally accepted that when a cataract-impaired lens is surgically extracted, smaller incisions in the eyeball cause less chance of postoperative astigmatism.

Accordingly, a technique called KPE (Kelman's pharmacoemulsification; suction of lens substance crushed by ultrasonic emulsification) using an ultrasonic emulsification/ suction apparatus has been developed. With this apparatus, an opaqued lens is crushed and emulsified by ultrasonication, and then sucked for removal. This technique permits an operation in which lenses are extracted through a small incision of approximately 4 mm, as compared to larger incisions of about 10 mm according to the conventional ECCE operation technique (extracapsular cataract extraction).

In connection with the technique which made small incisions possible as mentioned above, intraocular lenses which can be inserted through a small incision have been developed. Conventional intraocular lenses have an optical part made of a hard material such as glass or plastic; and, therefore, the incisions prepared at the time of transplant are greater than the diameter of the optical part which are in most cases 6.5 mm or more. Accordingly, even though a lens is extracted through a small incision according to the KPE technique, it is necessary that the incision be enlarged when a hard intraocular lens is inserted.

To solve this problem, Japanese Patent Application No. S58-1800S (Japanese Patent Application Laid-open (kokai) No. 146346/1983 Japanese Patent Publication No. H5-58748) discloses a deformable intraocular lens which can be inserted through a small incision made in an eyeball.

FIG. 4 (Prior Art) to FIG. 6 (Prior Art) show such an intraocular lens. It is made of an elastic material having predetermined memory characteristics. The thickness of the peripheral portion of the optical part of the lens is smaller than that of the central portion, and anchors 4a of a plurality of supports 4 which hold the optical part 3 within the eye and which are made of a different material from the optical part 3 are embedded at two positions on the periphery of the optical part 3 for bonding the supports to the optical part. The optical part 3 is integrally formed with a lens 3b which has an increased thickness from the periphery toward the center and a thin annular peripheral portion 3a which surrounds the lens 3b.

The optical part 3 can be deformed by rolling, bending, extending or folding to reduce its size. Therefore, an intraocular lens having such an optical part can be inserted through a small incision prepared in the eyeball with a newly developed applicator which can deform the optical part. With this applicator, the intraocular lens can be inserted through a small incision of about 4 mm in diameter, and can be restored to its original larger shape within the eye, based on the memory characteristics of the optical part 3. Thus, neither the size of the intraocular lens itself nor the method of inserting the lens requires the creation of a large incision.

In order to carry out an insertion of the above-described intraocular lens through a smaller incision using an applicator, the size of the object to be inserted, i.e., the deformable intraocular lens, is preferably as small as possible. In particular, the optical part, which affects the ease of the deforming operation, is desired to be minimized in size by making the thickness of the central part of the optical part smaller, and it is desired to reduce the size of the applicator by achieving a smaller thickness of the central portion.

In the conventional deformable lenses as described above, however, when the thickness of the center of the optical part is reduced, the periphery thereof becomes thinner accordingly. This is unfavorable because the anchors of the supports have to be embedded in a thin periphery portion of the optical part, which causes weak bonding strength between the supports and the optical part, poor supporting power of the supports, and reduced pull-off strength of the anchors. Thus, improved deformable intraocular lenses are still desirable.

SUMMARY OF THE INVENTION

The present invention addresses the above-mentioned problems by providing a deformable intraocular lens which has a thin deformable optical part, which can be inserted in the eye through a smaller incision than conventional incisions, and which does not weaken the bonding strength between the supports and the optical part.

According to the present invention, there is provided a deformable lens comprising an optical part which is made of an elastic material having predetermined memory characteristics and which has a thin periphery and a thick center, a plurality of supports which are made of a flexible material different from the material of the optical part and which have anchors embedded in the optical part for bonding the support to the optical part, wherein a plurality of reinforcing sections having a thickness larger than the periphery of the optical part are provided at a plurality of peripheral portions of the optical part, and the anchors of the supports are embedded in the reinforcing sections or in a lens at a slightly inner position toward the center of the lens.

DESCRIPTION OF THE PREFERRED EMBODIMENTS

The present invention will now be described by way of an embodiment while referring to the accompanying drawings.

Figure 1:
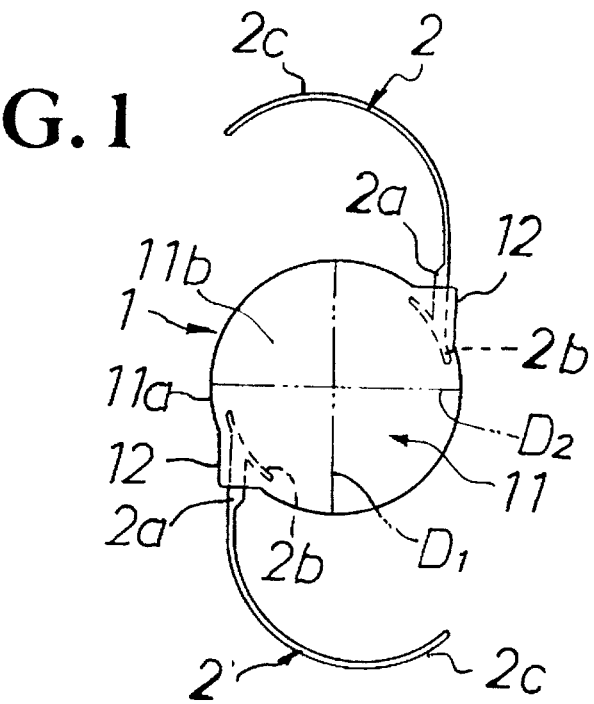
FIG. 1 is a plan view showing a deformable intraocular lens according to an embodiment of the present invention.
Figure 2:
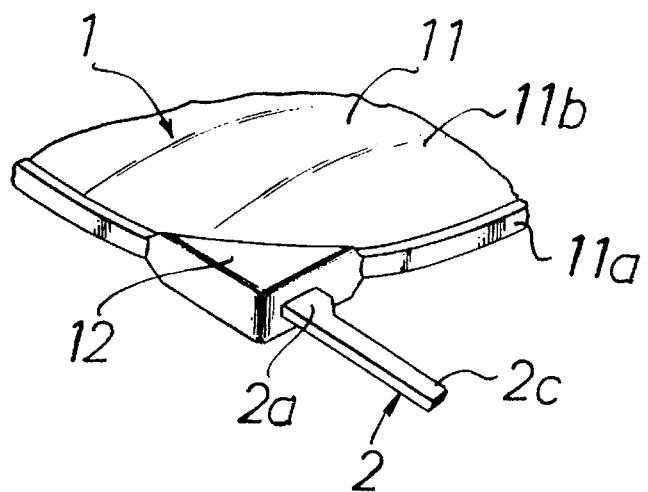
FIG. 2 is an enlarged perspective view of a portion of FIG. 1.
Figure 3:
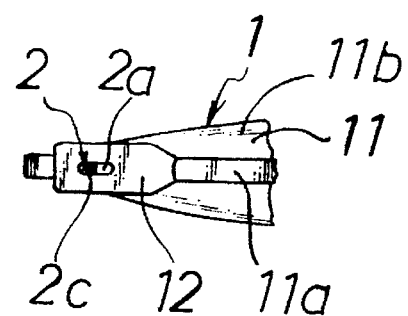
FIG. 3 is an enlarged front view of the region shown in FIG. 1.
Figure 4:
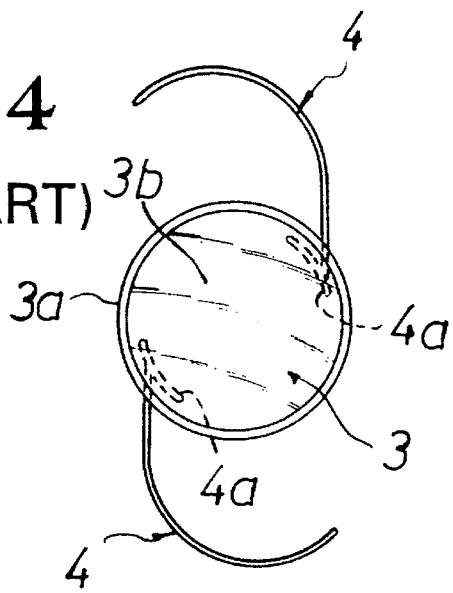
FIG. 4 (Prior Art) is a plan view showing a deformable intraocular lens according to the prior art.
Figure 5:
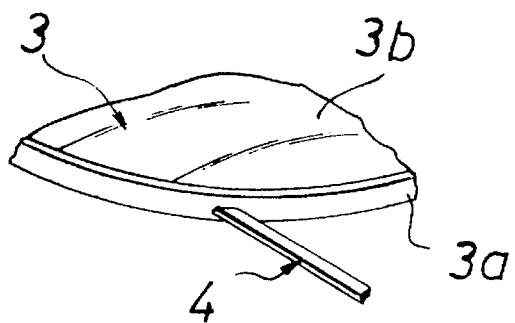
FIG. 5 (Prior Art) is an enlarged perspective view of a portion of the lens of FIG. 4.
Figure 6:
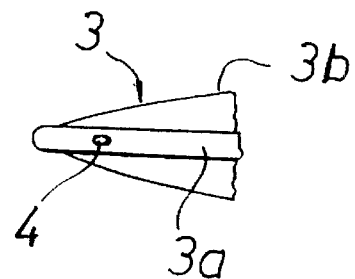
FIG. 6 (Prior Art) is an enlarged front view of the region shown in FIG. 4.

In FIGS. 1, 2 and 3, numeral 1 denotes an optical part made of a molded elastic material which is deformable and which has predetermined memory characteristics, and numeral 2 denotes a support made of a flexible material which is different from the material used for the optical part.

The optical part 1 is composed of a main section 11 having a disk shape and reinforcing sections 12. The main section 11 has a thin annular peripheral portion 11a and a lens portion 11b which is positioned in the central portion of the peripheral portion 11a and which has a gradually increasing thickness toward its center. In the present invention, the thickness at the center of the lens portion 11b, i.e., the center of the main section 11, is reduced compared to the aforementioned conventional lens.

The reinforcing sections 12 are disposed at two positions on the periphery of the main section 11, i.e., the right-upper position and the left-lower position in FIG. 1, and form approximately a right angle at each of the protruding corners. The reinforcing sections are disposed symmetrically with regard to the center of the main section 11. Moreover, as shown in FIGS. 2 and 3, the reinforcing section 12 is extended, from outside of the main section 11 to the outer periphery of the lens section 11b, in a uniform thickness which is thicker than the thickness of the outer periphery 11a of the main section 11. Both the reinforcing section and the peripheral portion may be generally bisected simultaneously by a plane. Furthermore, the reinforcing section and the peripheral portion are connected at an arc-shaped region having a first curvature, and wherein the anchor is arc-shaped with a second curvature, the first curvature being approximately equal to the second curvature.

The reinforcing sections 12, 12 are disposed within a circumscribed square of the lens having sides each corresponding to D1 or D2. The two sides of the reinforcing section 12 form a right angle in parallel to the diameters of the lens D1 and D2 shown in FIG. 1.

Each of the supports 2, 2 is composed of a base 2a which is relatively wide and thick, an anchor 2b which is integrally formed with the base 2a at one end thereof, and a tail 2c which has a small width and which is integrally connected to the base 2a at the other end thereof.

Two supports 2, 2 are provided as facing each other with the lens part 11b between them to form the optical part 1. The substantial part of the base 2a and the anchor 2b are embedded in and bonded to the lens 11b at a position in an area defined by the reinforcing section 12 and a slightly inner periphery toward the center of the lens 11b. The outer periphery of the base 2a is extended in parallel to one side of the reinforcing section 12 as shown in FIG. 1, and one end of the base 2a is slightly protruded outside of the other side of the reinforcing section 12.

The tail 2c of the support 2 has a spring function of a certain spring force which permits easy deformation by external force. The portion remote to the base 2a is bent to form a bulged arc as shown in FIG. 1. The ends of the tail 2c are symmetrically disposed with regard to the center of the lens 11b.

The optical part 1 is made of a transparent elastic material such as polyurethane elastomers, silicone elastomers, hydrogel polymers, collagen compounds, etc. The support 2 is made of a flexible synthetic resin such as polyimides.

The deformable intraocular lens of the above described embodiment is transplanted in the eye with a suitable device such as an applicator similar to that shown in Japanese Patent Application No. H3-142067C Japanese Patent Application Laid-open (kokai) No. 45-103803, by bending the optical part 1 in a tubular form parallel to the diameter D1 or D2 of the main section 11, and inserting it in place of the natural lens which has been extracted through a small incision, and allowing it to restore the original shape before deformation according to the memory characteristics of the optical part 1.

According to the present invention, the thickness of the central part of the optical part 1 which affects the ease of the deforming operation such as bending to the optical part 1 as described above, i.e., the thickness of the center of the lens 11 is made thinner than the thickness of the central part of conventional optical parts. Therefore, the diameter of the deformed tubular optical part can be made smaller as compared to the conventional ones. Thus, the intraocular lens according to the present invention can be inserted in the eye through a smaller incision of less than 4 mm, which is smaller than conventional incisions.

Moreover, although the thickness of the annular peripheral portion 11a of the main section 11 is inevitably reduced in accordance with the reduction of the thickness at the center of the optical part 1, the bonding strength between the support 2 and the optical part 1 is enhanced, the supportive function of the support 2 is improved, and the pull-off force of the support 2 is also increased.

In the above embodiment of the present invention, since the two reinforcing sections are protruded from the outer periphery of the main section of the optical part, the substantial part of the base of the support and the anchor may be embedded for bonding in these reinforcing sections.

As described above, the deformable intraocular lens according to the present invention has a structure which comprises an optical part which is made of an elastic material having predetermined memory characteristics and which has a thin periphery and a thick center, a plurality of supports which are made of a flexible material different from that of the optical part and which have anchors embedded in the optical part for bonding the support to the optical part, wherein a plurality of reinforcing sections having a thickness larger than the thin periphery of the optical part are provided at a plurality of peripheral portions of the optical part, and the anchors of the supports are embedded in the reinforcing sections or in a lens at a slightly inner position toward the center of the lens. With this structure, the deformable intraocular lens according to the present invention achieves the following effects.

Since the reinforcing sections which are thicker than the outer periphery of the optical part, are provided at a plurality of positions on the periphery of the deformable optical part, and the anchors of the supports are embedded in and bonded to the lens 11b at a position in an area defined by the reinforcing section 12 and a slightly inner periphery toward the center of the lens 11b, even when the thickness of the periphery is reduced, the bonding strength between the support and the optical part is not reduced, thereby preventing the supporting power of the support from being lowered, and preventing the pull-off force of the support from being reduced.

When the thickness of the periphery of the optical part is reduced, the entire optical part except the reinforcing section can be made thinner, including the center of the optical part. Accordingly, the optical part is deformed by bending or rolling to have a smaller shape and inserted in the eye through a small incision, and thereafter the original shape of the optical part before deformation is restored within the eye. Therefore, the intraocular lens according to the present invention can be easily inserted in the eye through a incision smaller than 4 mm by the use of an applicator which can deform the optical part into a small size.

What is claimed is:

1. A deformable intraocular lens comprising:

(a) an optical part made of an elastic material having predetermined memory characteristics, the optical part having (i) a lens portion, (ii) a peripheral portion surrounding the lens portion, and (iii) a plurality of reinforcing sections, each reinforcing section radially protruding from the peripheral portion, each reinforcing section being thicker than the peripheral portion; and (b) a plurality of supports, the supports being made of a flexible material different than the elastic material, each support being associated with a corresponding one of said reinforcing sections, each support having an anchor embedded in the optical part, each support having a portion embedded in the reinforcing section, each support having another portion protruding from the reinforcing section.

2. A deformable intraocular lens as claimed in claim 1, wherein the peripheral portion has a top surface and a bottom surface, and wherein the reinforcing section has an upper surface and a lower surface, a first distance being defined between the upper and lower surfaces of the reinforcing section, a second distance being defined between the lower surface of the reinforcing section and a plane containing the tip surface of the peripheral portion, a third distance being defined between the upper surface of the reinforcing section and a plane containing the bottom surface of the peripheral portion, the first distance being greater than the second distance, the first distance being greater than the third distance.

3. A deformable intraocular lens as claimed in claim 2, wherein the second distance is approximately equal to the third distance.

4. A deformable intraocular lens as claimed in claim 1, wherein both the reinforcing section and the peripheral portion may be generally bisected simultaneously by a plane.

5. A deformable intraocular lens as claimed in claim 1, wherein the radially protruding reinforcing section forms approximately a right angle.

6. A deformable intraocular lens as claimed in claim 2, wherein the radially protruding reinforcing section forms approximately a right angle.

7. A deformable intraocular lens as claimed in claim 3, wherein the radially protruding reinforcing section forms approximately a right angle.

8. A deformable intraocular lens as claimed in claim 4, wherein the radially protruding reinforcing section forms approximately a right angle.

9. A deformable intraocular lens as claimed in claim 1, wherein the reinforcing section and the peripheral portion are connected at an arc-shaped region having a first curvature, and wherein the anchor is arc-shaped with a second curvature, the first curvature being approximately equal to the second curvature.

10. A deformable intraocular lens as claimed in claim 2, wherein the reinforcing section and the peripheral portion are connected at an arc-shaped region having a first curvature, and wherein the anchor is arch-shaped with a second curvature, the first curvature being approximately equal to the second curvature.

11. A deformable intraocular lens as claimed in claim 3, wherein the reinforcing section and the peripheral portion are connected at an arc-shaped region having a first curvature, and wherein the anchor is arc-shaped with a second curvature, the first curvature being approximately equal to the second curvature.

12. A deformable intraocular lens as claimed in claim 4, wherein the reinforcing section and the peripheral portion are connected at an arc-shaped region having a first curvature, and wherein the anchor is arc-shaped with a second curvature, the first curvature being approximately equal to the second curvature.

13. A deformable intraocular lens as claimed in claim 5, wherein the reinforcing section and the peripheral portion are connected at an arc-shaped region having a first curvature, and wherein the anchor is arc-shaped with a second curvature, the first curvature being approximately equal to the second curvature.

14. A deformable intraocular lens as claimed in claim 6, wherein the reinforcing section and the peripheral portion are connected at an arc-shaped region having a first curvature, and wherein the anchor is arc-shaped with a second curvature, the first curvature being approximately equal to the second curvature.

15. A deformable intraocular lens as claimed in claim 8, wherein the reinforcing section and the peripheral portion are connected at an arc-shaped region having a first curvature, and wherein the anchor is arc-shaped with a second curvature, the first curvature being approximately equal to the second curvature.

16. A deformable intraocular lens as claimed in claim 1, wherein the elastic material of the optical part is a transparent elastic material selected from the group consisting of polyurethane elastomers, silicone elastomers, hydrogel polymers, and collagen compounds.

17. A deformable intraocular lens as claimed in claim 4, wherein the elastic material of the optical part is a transparent elastic material selected from the group consisting of polyurethane elastomers, silicone elastomers, hydrogel polymers, and collagen compounds.

18. A deformable intraocular lens as claimed in claim 9, wherein the elastic material of the optical part is a transparent elastic material selected from the group consisting of polyurethane elastomers, silicone elastomers, hydrogel polymers, and collagen compounds.

19. A deformable intraocular lens as claimed in claim 12, wherein the elastic material of the optical part is a transparent elastic material selected from the group consisting of polyurethane elastomers, silicone elastomers, hydrogel polymers, and collagen compounds.

20. A deformable intraocular lens as claimed in claim 19, wherein the flexible material of the supports is a synthetic resin.

\* \* \* \* \*